United States Patent [19]

Bibbs et al.

[11] Patent Number: 5,503,989
[45] Date of Patent: Apr. 2, 1996

[54] PRODUCTION OF PEPTIDE AMIDES

[75] Inventors: Jeffrey A. Bibbs, San Diego; Laura S. Lehman De Gaeta, Olivenhain; Howard Jones, Poway, all of Calif.

[73] Assignee: Amylin Pharmaceuticals, Inc., San Diego, Calif.

[21] Appl. No.: 927,755

[22] Filed: Aug. 10, 1992

Related U.S. Application Data

[63] Continuation-in-part of Ser. No. 742,768, Aug. 8, 1991, abandoned, and a continuation-in-part of Ser. No. 742,769, Aug. 8, 1991, abandoned.

[51] Int. Cl.$^6$ .............................. C12P 21/06; C07K 5/00; C07K 7/00; C07K 17/00
[52] U.S. Cl. .................. 435/68.1; 530/307; 530/309; 530/313; 530/317; 530/324; 530/345
[58] Field of Search ..................... 530/324, 345, 530/307, 317, 313, 309; 435/68.1

[56] References Cited

U.S. PATENT DOCUMENTS

| | | |
|---|---|---|
| 3,674,844 | 7/1972 | Shen et al. . |
| 3,904,593 | 9/1975 | Immer et al. . |
| 4,173,563 | 11/1979 | Yamazaki et al. . |
| 4,388,312 | 6/1983 | Terao et al. ............................ 424/244 |
| 4,442,029 | 4/1984 | Marguarding et al. . |
| 4,533,554 | 8/1985 | Terao et al. ............................ 514/464 |
| 4,709,014 | 11/1987 | Tamaoki ................................. 530/333 |
| 4,806,473 | 2/1989 | Johansen et al. ........................ 435/71 |
| 4,997,950 | 3/1991 | Murphy et al. ........................ 548/303 |
| 5,064,767 | 11/1991 | Le et al. ................................ 436/89 |
| 5,198,418 | 3/1993 | Malabarba et al. ........................ 514/8 |

OTHER PUBLICATIONS

Morrison & Boyd, Organic Chem. 3rd ed. p. 603, 1973.

Glazer et al. Chem. modification of proteins, eds. Work & Work, 1985 pp. 88–89.

*Primary Examiner*—Jill Warden
*Assistant Examiner*—Sheela J. Huff
*Attorney, Agent, or Firm*—Lyon & Lyon

[57] ABSTRACT

Methods of preparing a peptide having a C-terminal amide group from peptides having a C-terminal carboxyl group are provided.

12 Claims, 2 Drawing Sheets

FIGURE 1

Amylin KCNTATCATQRLANFLVHSSNNFGAILSSTNVGSNTY-NH₂

FIGURE 2

| | K | C | N | T | A | T | C | A | T | Q | R | L | A | N | F | L | V | H | S | S | N | N | F | G | A | I | L | S | S | T | N | V | G | S | N | T | Y | NH$_2$ |
|---|---|---|---|---|---|---|---|---|---|---|---|---|---|---|---|---|---|---|---|---|---|---|---|---|---|---|---|---|---|---|---|---|---|---|---|---|---|---|
| HUMAN | K | C | N | T | A | T | C | A | T | Q | R | L | A | N | F | L | V | H | S | S | N | N | F | G | A | I | L | S | S | T | N | V | G | S | N | T | Y | NH$_2$ |
| BABOON | - | - | - | - | - | - | - | - | - | - | - | - | - | - | - | - | - | - | - | - | - | - | - | - | - | - | - | - | - | - | - | - | - | - | - | - | - | NH$_2$ |
| MONKEY | - | - | - | - | - | - | - | - | - | - | R | - | - | - | - | - | - | - | - | - | - | - | - | - | T | - | - | - | - | - | - | - | - | - | D | - | - | NH$_2$ |
| CAT | - | - | - | - | - | - | - | - | - | - | R | - | - | - | - | - | - | - | - | - | - | - | - | - | - | - | L | - | - | P | - | - | - | - | - | - | - | NH$_2$ |
| DOG | - | - | - | - | - | - | - | - | - | - | R | T | - | - | - | - | - | - | - | - | - | - | - | - | - | - | L | - | - | P | - | - | - | - | - | - | - | NH$_2$ |
| RAT | - | - | - | - | - | - | - | - | - | - | R | - | - | - | - | - | - | - | - | - | - | - | - | - | - | P | V | - | - | P | P | - | - | - | - | - | - | NH$_2$ |
| MOUSE | - | - | - | - | - | - | - | - | - | - | R | - | - | - | - | - | - | - | - | - | - | - | - | - | - | P | V | - | - | P | P | - | - | - | - | - | - | NH$_2$ |
| HAMSTER | - | - | - | - | - | - | - | - | - | - | - | - | - | N | - | - | - | - | - | - | - | - | - | - | - | P | V | - | - | P | - | - | - | - | - | - | - | NH$_2$ |
| GUINEA PIG | - | - | - | - | - | - | - | - | - | - | - | - | T | - | - | - | - | - | - | - | - | - | - | - | R | H | L | - | - | A | - | L | P | - | D | - | - | NH$_2$ |
| DEGU | - | - | - | - | - | - | - | - | - | - | - | - | T | - | - | - | - | - | - | - | - | - | - | - | R | H | L | - | - | A | - | P | P | - | K | - | - | -NH$_2$ |

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
       ( A ) LENGTH: 34 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:1:

Lys Cys Asn Thr Ala Thr Cys Ala Thr Gln Arg Ala Asn Phe Val His
 1               5                  10                  15
Ser Ser Asn Asn Phe Gly Ala Ile Ser Ser Thr Asn Val Gly Ser Asn
                20                  25                  30
Thr Tyr ( 2 ) INFORMATION FOR SEQ ID NO:2:

( i ) SEQUENCE CHARACTERISTICS:
       ( A ) LENGTH: 34 amino acids
       ( B ) TYPE: amino acid
       ( C ) STRANDEDNESS: single
       ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

Lys Cys Asn Thr Ala Thr Cys Ala Thr Gln Arg Ala Asn Phe Val His
1               5                   10                      15

Ser Ser Asn Asn Phe Gly Ala Ile Ser Ser Thr Asn Val Gly Ser Asn
            20                  25                  30

Thr Tyr ( 2 ) INFORMATION FOR SEQ ID NO:3:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:3:

Lys Cys Asn Thr Ala Thr Cys Ala Thr Gln Arg Ala Asn Phe Val Arg
1               5                   10                      15

Ser Ser Asn Asn Phe Gly Thr Ile Ser Ser Thr Asn Val Gly Ser Asp
            20                  25                  30

Thr Tyr ( 2 ) INFORMATION FOR SEQ ID NO:4:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:4:

Lys Cys Asn Thr Ala Thr Cys Ala Thr Gln Arg Ala Asn Phe Ile Arg
1               5                   10                      15

Ser Ser Asn Asn Gly Ala Ile Ser Pro Thr Asn Val Gly Ser Asn Thr
            20              25                  30

Tyr ( 2 ) INFORMATION FOR SEQ ID NO:5:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:5:

Lys Cys Asn Thr Ala Thr Cys Ala Thr Gln Arg Ala Asn Phe Val Arg
1               5                   10                  15

Thr Ser Asn Asn Gly Ala Ile Ser Pro Thr Asn Val Gly Ser Asn Thr
            20              25                  30

Tyr ( 2 ) INFORMATION FOR SEQ ID NO:6:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:6:

Lys Cys Asn Thr Ala Thr Cys Ala Thr Gln Arg Ala Asn Phe Val Arg
1               5                   10                  15

Ser Ser Asn Asn Gly Pro Val Pro Pro Thr Asn Val Gly Ser Asn Thr
            20              25                  30

Tyr ( 2 ) INFORMATION FOR SEQ ID NO:7:

( i ) SEQUENCE CHARACTERISTICS:
        ( A ) LENGTH: 33 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:7:

Lys Cys Asn Thr Ala Thr Cys Ala Thr Gln Arg Ala Asn Phe Val Arg
1               5                   10                  15

Ser Ser Asn Asn Gly Pro Val Pro Pro Thr Asn Val Gly Ser Asn Thr
            20              25                  30

Tyr ( 2 ) INFORMATION FOR SEQ ID NO:8:

( i ) SEQUENCE CHARACTERISTICS:
        ( A ) LENGTH: 33 amino acids
        ( B ) TYPE: amino acid ( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:8:

```
Lys Cys Asn Thr Ala Thr Cys Ala Thr Gln Arg Ala Asn Phe Val His
 1               5                  10                  15
Ser Asn Asn Asn Gly Pro Val Ser Pro Thr Asn Val Gly Ser Asn Thr
                20                  25                  30
Tyr
```

( 2 ) INFORMATION FOR SEQ ID NO:9:

( i ) SEQUENCE CHARACTERISTICS:
( A ) LENGTH: 32 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:9:

```
Lys Cys Asn Thr Ala Thr Cys Ala Thr Gln Arg Thr Asn Phe Val Arg
 1               5                  10                  15
Ser Ser His Asn Gly Ala Ala Pro Thr Asp Val Gly Ser Asn Thr Tyr
                20                  25                  30
```

( 2 ) INFORMATION FOR SEQ ID NO:10:

( i ) SEQUENCE CHARACTERISTICS:
( A ) LENGTH: 33 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:10:

```
Lys Cys Asn Thr Ala Thr Cys Ala Thr Gln Arg Thr Asn Phe Val Arg
 1               5                  10                  15
Ser Ser His Asn Gly Ala Ala Pro Pro Thr Lys Val Gly Ser Asn Thr
                20                  25                  30
Tyr
```

PRODUCTION OF PEPTIDE AMIDES

RELATED APPLICATIONS

This application is a continuation-in-part of U.S. patent application Ser. No. 07/742,768, filed Aug. 8, 1991, now abandoned, and is also s continuation-in-part of U.S. patent application Ser. No. 07/742,769, filed Aug. 8, 1991, now abandoned.

BACKGROUND OF THE INVENTION

Only small quantities of certain peptides, including human amylin, are available from procedures which involve natural isolation. Amylin is a 37 amino acid peptide hormone which was recently discovered, isolated and purified by Cooper and Willis. European Patent Application No. 88303803.6 ("Amyloid Peptides"). Cooper also determined that amylin has marked effects on carbohydrate metabolism. See, e.g., Cooper et al., *Proc. Nat. Acad. Sci. USA* 84:8628–8632 (1987). Various patent applications relating to uses of amylin, amylin agonists, and amylin antagonists for the treatment of certain disorders, such as diabetes, have been prepared. European Patent Application No. 88307927.9 ("Use of Amylin or CGRP for the Treatment of Diabetes Mellitus"); International Application No. PCT/US89/00049 ("Treatment of Type 2 Diabetes Mellitus"). Commonly assigned and co-pending patent application U.S. Ser. No. 667,040 is directed to the synthesis of this amylin using a solid phase resin synthetic method. The application describes the synthesis of this hormone using solid phase methods which makes it available in greater quantities for extensive research, including anticipated clinical trials.

However, even conservative estimates as to the commercial requirements of amylin lead to the conclusion that about 50 to 500 kg will be needed annually. The largest protein to date made commercially by solid phase resin synthesis is salmon calcitonin which has 32 amino acids and which is synthesized on a scale of about 10 kg/year. The labors of synthesis increase geometrically with increased amino acid chain length; thus, synthesis of a 37 amino acid peptide is more formidable than a 32 amino acid peptide. Also the particular amino acid residue content of amylin may increase the burdens of synthesis using solid-phase methods. For the above reasons, options other than resin synthesis may be of value for larger scale synthesis of more complex proteins like amylin. As the requirements for larger and larger amounts of end product grow, equipment limitations and costs of amino acids and other reagents, along with waste disposal can make such synthesis procedures technically difficult and prohibitively expensive.

Recombinant DNA techniques may provide an attractive approach to the synthesis of amylin in commercial amounts. Some large proteins are now made commercially by this methodology (e.g., α-interferon, interleukin-2, tissue plasminogen activator, Factor VIII:C, erythropoietin). However, high levels of expression of these proteins by such biological systems are required to make their manufacture, isolation and purification commercially feasible. *E. coli* and yeast expression systems are capable of providing high yields of proteins by recombinant technology; however, these systems are not capable of performing certain post-translation modifications. For example, they do not construct or express peptide amides, only peptide acids. Amylin is a peptide amide that is much less biologically active in its peptide acid form. A few recombinant expression systems have been reported to provide the amide form of a precursor peptide acid; however, the recombinant expression systems that do provide the amide form of proteins, such as mammalian cells and the baculovirus expression vector system, do so in low yields. These yields would be too low to efficiently and economically provide the commercial quantities of amylin that would be required.

Several methods of enzymatic transformation of "protein precursor acids" to give a peptide amide have been described. Use of an α-amidating enzyme system isolated from rat medullary thyroid carcinomas to prepare an α-amidated polypeptide from a polypeptide substrate having a C-terminal glycine residue has been reported by one group. See Beaudry, G. A. et al., Journal of Biological Chemistry 265:(29):17694–17699 (1990); and U.S. Pat. No. 4,708,934. The amide function is reportedly donated to the polypeptide by cleavage from the α-amino group of the terminal glycine residue of a precursor polypeptide acid. The resulting α-amidated peptide has one less amino acid residue, the glycine residue having been eliminated.

This enzymatic amidation has proved difficult to reproduce and yields of product decrease exponentially as the size of the protein to be amidated is increased. The cost of the enzyme by natural extraction renders this process economically unacceptable on commercial scale, and the α-amidating enzyme has now been cloned, expressed, synthesized, and isolated by recombinant techniques. However, the use of the recombinantly synthesized enzyme on a precursor polypeptide having a C-terminal glycine acid added to the sequence which itself has been made by recombinant technologies would make the resulting process still unacceptably expensive for very large scale production of amylin (i.e., in the 500 kilogram per year synthesis scale).

Other enzymatic transformations reported to give protein amides involve proteases. One such method was said to convert small peptides to peptide amides using carboxypeptidase II. Klaus Breddam, Carlsberg, Res. Comm. Vol 50, p. 209 (1985). Another method was reported to generate peptides having a C-terminal amide using carboxypeptidase Y and small peptides, and in one case, human calcitonin-Leu. Most yields with this method were reported to be less than 25% (see U.S. Pat. No. 4,709,014, assigned to Sankyo Company Limited), and yields of peptide amides using such enzyme systems have been reported to decrease as the complexity or length of the peptide chain increases.

Aside from amylin, other peptide amides having biological activity include thyrotropin releasing hormone (TRH), oxytocin, vasopressin, luteinizing hormone releasing hormone, melanocyte stimulating hormone (MSH), gastrin, CGRP-1, CGRP-2, Substance P, secretin, the calcitonins, growth hormone releasing hormone, and vasoactive intestinal peptide (VIP).

Thus, it is important to provide an economically attractive and technically simple route to transform protein acids to amides. Unfortunately, while simple chemical transformations of carboxylic acids to carboxamides are known, the reagents usually involved in such reactions may destroy the sensitive protein backbone. In addition, as the complexity of the peptide sequence and structure increases, competing reactions with other reactive groups in the amino acid side chains increase, and such side reactions may drastically reduce the yield of the desired peptide amide.

SUMMARY OF THE INVENTION

The present invention provides methods of preparing a peptide having a C-terminal amide group ("peptide amide")

from the corresponding peptide having a C-terminal carboxyl group ("peptide acid"). Thus, according to one aspect of the present invention a solution of a peptide acid is treated with a carboxyl activating agent to give a reactive intermediate. Suitable carboxyl activating agents include carbodiimide compounds. The reactive intermediate is then treated with a trapping agent and an amine source (which is the donor —NH$_2$) to give the peptide amide. According to a second, preferred, aspect of the invention, the peptide acid is treated with an alcohol in the presence of an acid to give a reactive intermediate different from that referred to above. This intermediate is then treated with an amine source to yield the peptide amide.

The methods of the present invention may be used to prepare a peptide amide from their corresponding peptide acids. Such peptide amides include amylin, such as human amylin, and amylin derivatives and analogs (whether full length or less than thirty-seven amino acids in length) which are amidated at their carboxy termini. They also include thyrotropin releasing hormone, oxytocin, vasopressin, luteinizing hormone releasing hormone, melanocyte stimulating hormone, gastrin, CGRP-1, CGRP-2, secretin, calcitonins (especially salmon, chicken, eel and human calcitonin), growth hormone, releasing hormone, vasoactive intestinal peptide, as well as analogs (including active analogs) of those peptide amides which will generally contain C-terminal fragments of not less than three amino acids.

According to the first aspect of the present invention described above, free amine groups of the peptide acid may be reversibly blocked using an amine-blocking reagent prior to treatment with the carboxyl activating agent. According to one preferred aspect, the free amines on the side chains of amino acids, such as lysine, are so protected by blocking groups, and if desired, the N-terminal α-amino group may also be protected.

According to another aspect of the present invention a peptide acid fragment (having n minus m amino acid residues, herein the complete peptide amide has n amino acids) is coupled to a peptide amide fragment (having m amino acid residues and a C-terminal amide group). This method is similar to the above method in that the reaction is carried out under coupling conditions in the presence of (1) a carboxyl activating agent and a trapping agent or (2) an acidic alcohol so that the peptide acid fragment and the peptide amide fragment are coupled to give the peptide amide.

According to another aspect of the present invention, a peptide amide is prepared from the corresponding peptide acid by esterifying all free acid groups (i.e., carboxyl groups), followed by specific conversion of the C-terminal carboxyl to an amide, and by hydrolysis or de-esterification (deprotection) of the side chain esters to acids. In one preferred aspect, where the starting peptide acid contains side chain carboxyl groups, the conversion of C-terminal ester to amide is accomplished using an enzyme selective for the C-terminal ester and an NH$_2$ source such as an amine or amino acid-amide. Useful enzymes for the preparation of amylin by this method include chymotrypsin, thermolysin, papain, pepsin, bromelain, and other enzymes which are specific for aromatic amino acids.

According to a preferred aspect of the present invention, amylin, a protein hormone containing a C-terminal amide (and which has also been referred to in the literature as amylin amide), is prepared from the corresponding amylin acid precursor. The present invention provides methods which result in the economical synthesis of amylin. Thus, an amylin precursor acid may be made by a high yielding yeast or E. coli recombinant expression system. The amylin acid is then used according to the methods of the present invention to yield the desired amylin. Thus, by using the methods of the present invention one can take advantage of the advantageous economics of such recombinant technology expression systems and then convert the peptide acid produced thereby to the corresponding amide.

Definitions

As used herein, the following terms have the following meanings, unless expressly stated to the contrary.

The term "peptide acid" refers to an oligopeptide, polypeptide or protein which has a C-terminal carboxyl group.

The term "peptide amide" refers to an oligopeptide, a polypeptide or a protein which has a C-terminal amide group.

The term "amylin acid" refers to an amylin polypeptide having a C-terminal carboxyl group (e.g., the amino acid sequence shown in FIG. 1 for human amylin where X is a C-terminal carboxyl group).

The term "amylin" refers to the amidated form of a species of amylin acid, for example, a polypeptide having the amino acid sequence of human amylin shown in FIG. 1 where X is a C-terminal amide group.

BRIEF DESCRIPTION OF THE DRAWINGS

FIG. 1 depicts the amino acid sequence of human amylin.

FIG. 2 depicts a comparison of amino acid sequences of amylins isolated from several different mammals.

DETAILED DESCRIPTION OF THE INVENTION

This invention provides methods by which a peptide acid, such as an amylin acid, can be converted to its corresponding amide form, i.e., amylin. Thus, according to a preferred aspect, the present invention provides methods to chemically prepare an amylin from an amylin acid. In general, one aspect of the present invention provides the protection of the free amine group(s) amylin acid by reversible blocking of those free amine group(s) before the actual coupling/amidation reaction takes place. An alternate aspect involves performing the coupling/amidation reaction without the protection of the amylin acid. In another aspect the present invention provides for the activation of the C-terminal carboxylate before amidation takes place. An alternate aspect involves performing the amidation without activation. Another aspect couples a peptide acid fragment and an amidated peptide fragment such as an amidated amino acid to give a peptide amide.

A. Direct Preparation of Peptide Amide from Peptide Acid

In one aspect, the present invention provides methods for preparing a peptide amide directly from a peptide acid. According to this aspect of the present invention a solution of peptide acid is treated with a serine hydrolase enzyme and an amine source. Suitable enzymes include carboxypeptidase Y or carboxypeptidase P. Suitable solvents include those solvents used traditionally with enzyme assisted reactions such as aqueous-organic mixture adjusted to apparent pHs. Suitable amine sources include previously amidated amino acids.

In another aspect, the invention provides methods for preparing a peptide amide directly from a peptide acid without requiring free amine protection where the peptide contains no acidic amino acid residues if the peptide acid contains acidic amino acid residues, it is preferred that those residues be protected. According to this aspect of the present invention a solution of peptide acid in solvent is treated with a carboxyl activating agent to give a reactive intermediate. Suitable carboxyl activating agents include carbodiimides such as 1-(3-dimethylaminopropyl)-3-ethylcarbodiimide, diisopropylcarbodiimide, and carbonyldiimidazole, as well as dicyclohexylcarbodiimide. Suitable solvents include solvents such as those conventionally used in peptide synthesis and solvents that tend to disrupt secondary structural elements and minimize formation of intramolecular and intermolecular hydrogen bonds. Suitable solvents include dimethylformamide (DMF), dimethylsulfoxide, tetrahydrofuran, N-methylpyrrolidone, and the like. The reactive intermediate which is an imide after treating with the carbodiimide is treated with a trapping agent and an amine source. Suitable trapping agents include N-hydroxybenzotriazole, N-hydroxysuccinimide, N-hydroxyphthalimide, N-hydroxyglutarimide, benzhydroxamic acid and hydroxypiperidine. Suitable amine sources include ammonia and hydrated forms of ammonia. According to a preferred aspect of the present invention, reagents are provided which act both as a trapping agent and as an amine source.

B. Preparation of Peptide Amides Using Protected Peptide Acids

In one embodiment the methods of the present invention include a first step in which the solution of peptide acid is treated with an amino-blocking reagent which reversibly blocks free amine groups to give a protected peptide acid. In one preferred aspect, free amine groups on the side chains of amino acids such as lysine are blocked. If desired the N-terminal α-amino group may also be blocked. Suitable blocking groups include t-butoxycarbonyl ("t-Boc" or "Boc"), N-fluorenylmethoxycarbonyl (Fmoc), acetyl, pivalloyl, butyl, benzoyl and benzyl. Where the blocking group employed is Boc, the protected peptide acid may be conveniently prepared using di-tert-butylcarbonate. Optionally, a step may be included wherein protected peptide acids are separated from unprotected peptide acids and/or side chain protected peptide acids are separated from fully protected peptide acids.

After protection of the free amines, the protected peptide acid is treated with a carboxyl activating agent, and, then, a trapping agent including the amine source as described in Section A herein above to give a protected peptide amide. The blocking groups are removed by conventional deblocking reagents and methods such as treatment with trifluoroacetic acid (TFA) to give the peptide amide. Optionally, the protected peptide amides may be separated from unamidated protected peptide acids prior to deprotection.

C. Preparation of Peptide Amide Via an Ester Intermediate

An alternate aspect of the present invention is directed to preparation of a peptide amide using an ester intermediate.

The peptide acid is treated with anhydrous or aqueous acid and alcohol to esterify all carboxylic acid groups. Suitable alcohols include short chain aliphatic alcohols such as methanol, ethanol, isobutanol, propanol, isopropanol, n-butanol or t-butanol to give the corresponding methyl, ethyl, isobutyl, propyl, isopropyl, n-butyl or t-butyl esters. The ester intermediate is then treated with an amine, such as ammonia, and a selective amidation reagent, preferably as an enzyme such as chymotrypsin to specifically (and selectively) convert the C-terminal ester group to an amide. Alternatively the ester intermediate is treated with an amino acid amide ($-NH_2$) and carboxypeptidase Y.

The side chain ester groups are removed by hydrolysis or deprotection (by a reagent such as TFA for t-butyl esters) to give the C-terminally amidated protein.

Alternatively, where the peptide acid has no carboxylic acid side chains, i.e., where the only carboxyl group of the peptide acid is the C-terminal carboxyl, the ester intermediate may be converted to the corresponding peptide amide by treatment with ammonium hydroxide, ammonia in methanol, or liquid ammonia. (see Example 9).

D. Preparation of Peptide Amide by Coupling a Peptide Ester Intermediate to a Peptide Amide Fragment According to this aspect of the present invention, a peptide amide (having n amino acid residues) is prepared by coupling a peptide ester fragment (having n minus m amino acid residues) to a peptide amide fragment (having m amino acid residues). This method is similar to those described herein above, however, the peptide ester fragment has fewer amino acid residues than the resulting peptide amide and the peptide amide fragment acts as an amine source. Preferred peptide amide fragments are amidated amino acids or amidated oligopeptides having up to about 15 to about 20 amino acid residues, more preferably about 1 to about 5 amino acid residues.

E. Preparation of Amylin Amide

In a first method according to the present invention, amylin acid may be converted to amylin by a one step reaction that does not include any type of protecting groups, that is, the free amines of the amylin acid are left exposed. This reaction comprises the chemical conversion of the amylin acid to amylin using the 1-(3-dimethylaminopropyl)-3-ethylcarbodiimide as the carboxyl activating agent and a trapping agent/amine source reagent in DMF. This reaction gave a yield of about 16% with the nonprotected amylin acid (see Example 7).

According to a second aspect of the present invention, there is provided a first step in which accessible free amines in the amylin acid are blocked using a blocking reagent such as di-tert-butyl dicarbonate. This reaction may proceed with an overall yield of >90%. A second step comprises the activation of the C-terminal carbonyl of the resulting protected amylin acid with a carboxyl activating agent such as 1-(3-dimethylaminopropyl)- 3-ethylcarbodiimide and then an amidation step using amidation reagents which comprises a trapping reagent such as N-hydroxybenzotriazole (HOBt) along with an amine source such as ammonia; alternatively the trapping agent and amine source may be combined as one amidation reagent such as ammonium N-hydroxysuccinimide, ammonium N-hydroxyphthalimide, ammonium N-hydroxyglutarimide, ammonium benzhydroxamic acid, or ammonium N-hydroxypiperidine. The activation and amidation reagents may be conveniently delivered to the reaction mixture at the same time. This reaction proceeds with about an 86% yield using the Boc-amylin acid as the starting peptide, and a 20% yield with the $Boc_2$-amylin acid. A third step comprises the deblocking of the Boc-amylin with TFA. This deblocking reaction can be carried out on either the isolated Boc-amylins or with the nonpurified crude Boc-amylins (Boc-amylin and $Boc_2$-amylin). The TFA-treatment of crude Boc-amylin did completely deblock the amylin. This was confirmed by reverse phase HPLC using an amylin standard coinjection.

Although the above method may include the step of separating the two Boc-amylin acids (i.e., Boc-amylin acid and $Boc_2$-amylin acid), this separation step is not necessary. Both protected peptide acids will be exposed to the same reagents for coupling and deprotection, and there is no need to isolate the individual protected peptide acids. Although some of intermediate products may be different, the last step from both routes (t-Boc deprotection) produces the same amylin peptide, thus eliminating isolation of the individual peptides. Therefore, the Boc-peptide acids can be combined and the reactions carried out together, saving both time and chemicals.

A third method according to the present invention is similar to the previously described procedures, except the nucleophile (or amine source) will be slightly larger (e.g., $Tyr-NH_2$-versus $NH_3$) and the corresponding starting peptide acid will have fewer amino acid residues (e.g., $amylin^{1-36}$ versus $amylin^{1-37}$). According to thins exemplification, first, $amylin^{1-36}$ acid is Boc-protected using methods such as those used for the protection of amylin acid described above. Then, the $Boc-amylin^{1-36}$ is coupled to $Tyr-NH_2$ using 1-(3-dimethyl-aminopropyl)- 3-ethylcarbodiimide and HOBt in DMF. Finally the Boc-amylin is deprotected with TFA treatment (see Example 8). According to this aspect of the present invention, amylin can be synthesized in many ways just by coupling one of any number of different peptide acid fragments with the appropriate peptide amide fragment.

Some of the above procedures utilize protocols involved in synthetic peptide chemistry. See, e.g., Bodanszky and Bodanszky, *The Practice of Peptide Synthesis*, (Springer-Verlag, 1984); *The Peptides Analysis, Synthesis, Biology*, Vol. 1, (Eds. Gross and Meienhofer, Academic Press, Inc., 1979). Activation and trapping reactions are used in solution phase as well as solid phase peptide chemistry. Suitable carboxyl activating agents include 1,3-dicyclohexylcarbodiimide (DCC), 1,3-diisopropylcarbodiimide, and carbonyldiimidazole. Suitable trapping agents include N-hydroxysuccinimide; N-hydroxyphthalimide; N-hydroxyglutarimide. Other common carboxyl activating agents and trapping agents are described in the above-noted references, the disclosures of which are incorporated herein by reference. Other suitable amine protecting groups which include chemically labile moieties such as a Fmoc protecting group may be used, along with the appropriate deprotection protocols and reagents conventionally used with those protecting groups.

To assist in understanding the present invention, the following examples are included which describe the results of a series of experiments. The following examples relating to this invention should not, of course, be construed as specifically limiting the invention, and such variations of the invention, now known or later developed, which would be within the purview of one skilled in the art are considered to fall within the scope of the invention as described herein and hereinafter claimed.

EXAMPLES

All materials used for these preparations were used as received, and no further purification was done. All water used for these experiments were purified through the Millipore "Milli-Q Water Purification System" (5 cartridge model). Fast atom bombardment analysis was carried out by M-Scan, Incorporated (West Chester, Pa). Mass calibration was performed using cesium iodide or cesium iodide/glycerol.

EXAMPLE 1

Preparation of Amylin from Amylin Acid

First, 250 μg of human amylin acid was dissolved in 60 μl of 0.4M tyrosine amide with 5mM EDTA at pH 5.5. Then 12 μg of carboxypeptidase Y was added and the reaction proceeded at room temperature. The reaction was monitored by HPLC to 15% yield of amylin.

EXAMPLE 2

Preparation of Amylin from a Peptide Acid

First, 250 μg of $amylin^{1-36}$ Ala-OH was dissolved in 60 μl of 0.4M with 5 mM EDTA of tyrosine amide already adjusted to pH 6.5. Then 12 μg of carboxypeptidase Y was introduced and the transamidation was allowed to proceed at room temperature. Amylin formation was monitored by HPLC in excess of 15%.

EXAMPLE 3

Preparation of Boc-Amylin Acid

One milligram of amylin acid (Bachem Bioscience, Lot # ZH714) was dissolved in 0.5 mL of water (in a 1.5 mL eppendorf tube, as glass is to be avoided). To this solution, 0.5 mL of dimethylformamide ("DMF," American Burdick & Jackson, High Purity Solvent grade) was introduced. Then to this mixture was added approximately 200 mg of di-tert-butyl dicarbonate (Aldrich Chemical Co.) and the resulting mixture was stirred at room temperature. The reaction progress was monitored by reverse-phase high performance liquid chromatography (HPLC) using a Waters 625 LC with a 486 Waters detector and a 712 Waters Intelligent Sample Processor (WISP). The mobile phases were 0.1% trifluoroacetic acid (TFA) in water (solvent A) and 0.1% TFA in acetonitrile (solvent D). The reverse-phase column was a Poros R/H column (4.6 mm×100 mm). The gradient used was a 20 to 40% solvent B in 15 minutes with flow rate of 3.0 mL/min. The acid starting material eluted at 7.34 minutes, the Boc-amylin acid eluted at 8.52 minutes, and the $Boc_2$-amylin acid eluted at 11.3 minutes. The products were collected and dried using a Savant Speedvac Concentrator. Mass spectral analysis suggested the two products formed were the Boc-amylin acid and $Boc_2$-amylin acid.]

EXAMPLE 4

Preparation of Boc-Amylin

The Boc-amylin acids prepared according to Example 3 are used as the starting material for the preparation of Boc-amylin.

First, the Boc-amylin acid (about 50μg) is dissolved in 200 μL of DMF, then 200 mg of 1-(3-dimethylaminopropyl)-3-ethylcarbodiimide (Aldrich Chemical Co. 98%) and 200 mg of a trapping agent/ammonium source is added. After all three components are combined, and the mixture is allowed to stir at room temperature. The reaction is carried out in a 1.5 mL eppendorf tube. This reaction is monitored by reverse-phase HPLC using the Waters system described in Example 3 but using a different column and solvent system. A Vydac C4-protein column (0.46 mm×25 mm) is used. The mobile phase is a 2% acetic acid/3.3% triethylamine (TEA) in water, pH 5.0 (solvent C) and 2% acetic acid/3.3% TEA in acetonitrile (solvent D). The gradient used for these analyses is 28 to 38% solvent D in 30 minutes at 1.0 mL/min. The starting material elutes at 20.5 minutes and the product Boc-amylin elutes at 22.3 minutes. After isolating (by HPLC collection) and drying the product (using a Speedvac Concentrator), mass spectral analysis is conducted to ensure that the product has the M+ ion expected for Boc-amylin.

EXAMPLE 5

Preparation of $Boc_2$-Amylin

The Boc-amylin acids prepared according to Example 3 are used as the starting material for the preparation of $Boc_2$-amylin.

In a 1.5 mL eppendorf tube, 50μg of $Boc_2$-amylin acid is dissolved with 200 μL of DMF. Then 200 mg of both 1-(3-dimethylaminopropyl)-3-ethylcarbodiimide and a trapping agent/amine source are added. The resulting mixture is allowed to stir at room temperature. The reactions are monitored by HPLC as described in Example 4, except the gradient is 28 to 43% solvent D in 45 minutes. The $Boc_2$-amylin acid starting material elutes at 34.5 minutes and the product $Boc_2$-amylin elutes at 37.0 minutes.

EXAMPLE 6

Preparation of Amylin from Boc-Amylin and $Boc_2$-amylin

The reactions described in Examples 4 and 5 were stopped and the solvents were removed by high vacuum. Then in small glass flask, 0.5 mL of 100% TFA was added and the solution vortexed for 5 minutes. Afterward, the TFA was pulled off and the reaction checked for deprotection. The solid was reconstituted in 6M guanidine hydrochloride; then reverse-phase HPLC was used to monitor progress. The mobile phase used for this analysis was the same as described in Example 4 (used for the analysis of the Boc-amylin formation), along with the same gradient and column. The Boc-amylin had an elution time of 22.5 minutes whereas the amylin product had an elution of 19.8 minutes. Product verification was carried out by spiking the sample with an amylin standard and observing coelution at 19.8 minutes. The amylin acid elution time was 16.6 minutes and some amylin acid was observed due to unreacted Boc-amylin acid present in Boc-amylin. Similar conditions were used for the deprotection of the $Boc_2$-amylin.

EXAMPLE 7

Preparation of Amylin from Amylin Acid

The conversion of acid to amide may be performed as one step, that is without protection of free amine groups. This reaction was carried out using nonprotected amylin acid according to the following procedure:

First 0.8 mg of amylin acid was dissolved in 1.0 mL of DMF. Then, 200 mg each of 1-(3-dimethylaminopropyl)-3-ethylcarbodiimide and a trapping agent/amine source were introduced. The resulting mixture was allowed to stir at room temperature. The progress of the reaction was monitored using reverse-phase HPLC. The mobile phases were solvents C and D as described in Example 4 above. The gradient was 28 to 38 percent solvent D in 30 minutes at 1 mL/minute. The amylin retention time was 19.8 minutes and the amylin acid elution time was 16.6 minutes. Amylin formation was confirmed using mass spectral analysis.

EXAMPLE 8

Preparation of Amylin via Peptide Coupling

First, the N-terminal peptide is protected by dissolving 1 mg of, for example, $amylin^{1-36}$ acid in 1 mL of a 1:1 mixture of water:DMF. To that mixture, 200 mg of di-tert-butyl dicarbonate is added and the reaction is allowed to stir at room temperature. The mono- and di-protected peptides are separated by reverse-phase HPLC methods similar to those used with the previously mentioned tBoc-protected peptides (see Examples 2 and 3). Then, 200 mg of 1-(3-dimethylaminopropyl)-3-ethylcarbodiimide and HOBt along with 0.5 g of $Tyr-NH_2$ are added and the reaction mixture is allowed to stir at room temperature. The reaction is monitored using HPLC as described for the previous couplings (see Examples 4 and 5). The Boc-amylin is then deprotected as described in Example 6.

EXAMPLE 9

Preparation of Amylin

A. Preparation of Amylin Methyl Ester

1. Hydrochloric acid (0.15N) in Methanol Treatment

A 0.15N solution of HCl in methanol was prepared by adding 10.5 mL of acetyl chloride (Aldrich Chemical Co.) to 1.0 mL of methanol (99.9%-Aldrich Chemical Co.). The solution is prepared only minutes before the esterification reaction.

A 19 mg aliquot of amylin acid was treated with 35 mL of the above 0.15N HCl solution. The mixture was allowed to stir at room temperature for 6 hours. After 5.75 hours, 59% of the amylin acid had converted to the corresponding methylester as determined by reverse-phase HPLC. After 14 additional hours of stirring, the reaction had gone to 66% methyl ester. After an additional 2 hours, the reaction had gone to 68% methyl ester and the mixture was worked up. The mixture was cooled down with ice and neutralized using N-methylmorpholine. The methanol was removed using high vacuum. The resulting solid was purified using reverse-phase HPLC to give 6–7 mg of a 99% pure amylin methyl ester, as confirmed with mass spectral analysis.

2. Hydrochloric Acid and Guanidine Hydrochloride in Methanol Treatment

First, 250 μg of amylin acid was dissolved in 250 μl of 0.13N HCl and 4M guanidine hydrochloride in methanol. As shown by HPLC this reaction had a yield of amylin acid of 90% in 160 minutes. This reaction was allowed to proceed at room temperature.

In either case, molecular sieves may be added to the reaction mixture to assist in removing water generated by the reaction or HCl which improves the percent of ester formed.

B. Conversion of Amylin Methyl Ester to Amylin

1. Ammonium Hydroxide Treatment

A 100 mL aliquot of the esterification reaction mixture from step A was removed. The HCl and methanol were blown off using UHP argon gas. The resulting ester/acid solid mixture was dissolved in 100 mL water; then 500 μL of 28–30% ammonium hydroxide (Aldrich Chemical Co.)

was added and the mixture was allowed to sit at room temperature. After three hours, HPLC indicated amylin formation, which was confirmed by mass spectral analysis.

Another reaction was carried out using 240 µg of purified amylin methyl ester! which was treated with 500 µL of cold 28–30% ammonium hydroxide. After thirty minutes at room temperature, HPLC analysis of the mixture indicated amylin formation. After 300 minutes, nearly all of the amylin methyl ester had disappeared, as determined by reverse phase HPLC.

2. Ammonia in Methanol Treatment

Purified amylin methyl ester, 240 µg was combined with 500 µL of 2N ammonia in methanol (Aldrich Chemical Co.). After 20 hours, amylin formation was observed, as indicated by reversephase HPLC, with very little peptide degradation.

3. Liquid Ammonia Treatment

Crude amylin methylester from above esterification (Example 5), 250 µg was combined with approximately 1 mL of liquid ammonia at −200° C. Then the peptide solution was allowed to reach room temperature for 20 minutes. The solution was then recooled to −200° C. then allowed to reach room temperature again but while the ammonia allowed to evaporate. By HPLC the ester was converted to the amylin amide in greater than 95% yield.

EXAMPLE 10

Conversation of Amylin Methyl Ester to Amylin Using Chymotrypsin

Purified amylin methyl ester was prepared as described in Example 9, Step A above.

Amylin methyl ester is treated with a nucleophile solution such as 0.57M ammonium acetate at a pH of between 4.8 and 6 in the presence of chymotrypsin. Generation of amylin is monitored using reverse phase HPLC.

We claim:

1. A method of preparing a peptide having a C-terminal amide which comprises:
   (a) treating a solution of a peptide acid form of said peptide with an esterifying reagent to esterify free carboxyl groups of the peptide acid to give a peptide ester; and
   (b) treating the peptide ester of step (a) with an $NH_2$ source and chymotrypsin to selectively convert the C-terminal ester group of the peptide ester to an amide group to give said peptide having a C-terminal amide group.

2. A method of preparing a peptide having a C-terminal amide which comprises:
   (a) treating a solution of a peptide acid form of said peptide with an esterifying reagent to esterify free carboxyl groups of the peptide acid to give a peptide ester; and
   (b) treating the peptide ester of step (a) with an $NH_2$ source and an enzyme selected from the group consisting of thermolysin, papain, pepsin and bromelain, to selectively convert the C-terminal ester group of the peptide ester to an amide group to give said peptide having a C-terminal amide group.

3. A method of preparing a peptide selected from the group consisting of an amylin, an amylin derivative and an amylin analog having a C-terminal amide which comprises:
   treating a solution of a peptide acid form of said peptide with an esterifying reagent to esterify free carboxyl groups of the peptide acid to give a peptide ester;
   (b) treating the peptide ester of step (a) with an $NH_2$ source and an amidation reagent which selectively converts the C-terminal ester group of the peptide ester to an amide group to give said peptide having a C-terminal amide group, wherein said amidation reagent comprises an enzyme which selectively converts the C-terminal ester group of the peptide ester to a C-terminal amide group; and
   (c) removing ester groups from side chain carboxyl groups to give said peptide having a C-terminal amide.

4. A method according to claim 3 wherein said $NH_2$ source is an amine and said enzyme is chymotrypsin.

5. A method according to claim 3 wherein said $NH_2$ source is an amine and said enzyme is selected from the group consisting of thermolysin, papain, pepsin, and bromelain.

6. A method according to claim 3 wherein said $NH_2$ source is an amino acid-amide and said enzyme is carboxypeptidase Y.

7. A method according to any of claims 3, 4 or 5 wherein said esterification reagent comprises an alcohol and acid.

8. A method according to any of claims 3, 4 or 5 wherein said peptide having a C-terminal amide is an amylin.

9. A method according to claim 8 wherein said amylin is human amylin.

10. A method according to claim 8 wherein said amylin is an analog of human amylin and contains a C-terminal amide group.

11. A method according to claim 6 wherein said peptide acid form is amylin$^{1-36}$gly-COOH.

12. A method according to claim 6 wherein said peptide acid form is amylin$^{1-36}$ala-COOH.

* * * * *